(12) United States Patent
Johnson

(10) Patent No.: US 6,386,971 B1
(45) Date of Patent: May 14, 2002

(54) AIR FRESHENER HOLDING DEVICE

(76) Inventor: Martha A. Johnson, 1279 Cummings Rd., Ridge Spring, SC (US) 29129

( * ) Notice: Subject to any disclaimer, the term of this patent is extended or adjusted under 35 U.S.C. 154(b) by 0 days.

(21) Appl. No.: 09/666,917

(22) Filed: Sep. 21, 2000

(51) Int. Cl.[7] .................................................. F24F 6/00
(52) U.S. Cl. ........................................ 454/328; 422/124
(58) Field of Search ................................ 454/328, 337, 454/157; 422/123, 124; 236/60

(56) References Cited

U.S. PATENT DOCUMENTS

| | | | | |
|---|---|---|---|---|
| 447,942 A | * | 3/1891 | Collins | ........................ 422/123 |
| 1,250,891 A | * | 12/1917 | Johnson | ........................ 454/368 |
| 3,119,649 A | * | 1/1964 | Mendolia | ..................... 454/368 |
| 4,523,870 A | | 6/1985 | Spector | |
| 4,944,898 A | | 7/1990 | Glaser | |
| 5,383,765 A | | 1/1995 | Baxter et al. | |
| 5,422,078 A | * | 6/1995 | Colon | ........................ 422/123 |
| 5,527,493 A | * | 6/1996 | McElfresh et al. | ........... 261/30 |
| 5,624,230 A | | 4/1997 | Taylor et al. | |
| 5,761,915 A | | 6/1998 | Rao | |
| 5,775,876 A | | 7/1998 | Walker et al. | |

* cited by examiner

*Primary Examiner*—Harold Joyce
*Assistant Examiner*—Derek Boles

(57) ABSTRACT

An air freshener holding device for evenly dispensing a fragrance throughout an entire room each time a fan unit is turned on. The air freshener holding device includes a container having a front wall, a back wall, a bottom wall, side walls, an open top, and a storage compartment being disposed therein and being adapted to removably retain cakes of deodorant; and also includes fastening members being attached to the container and being adapted to attach the container to a fan vent cover.

5 Claims, 2 Drawing Sheets

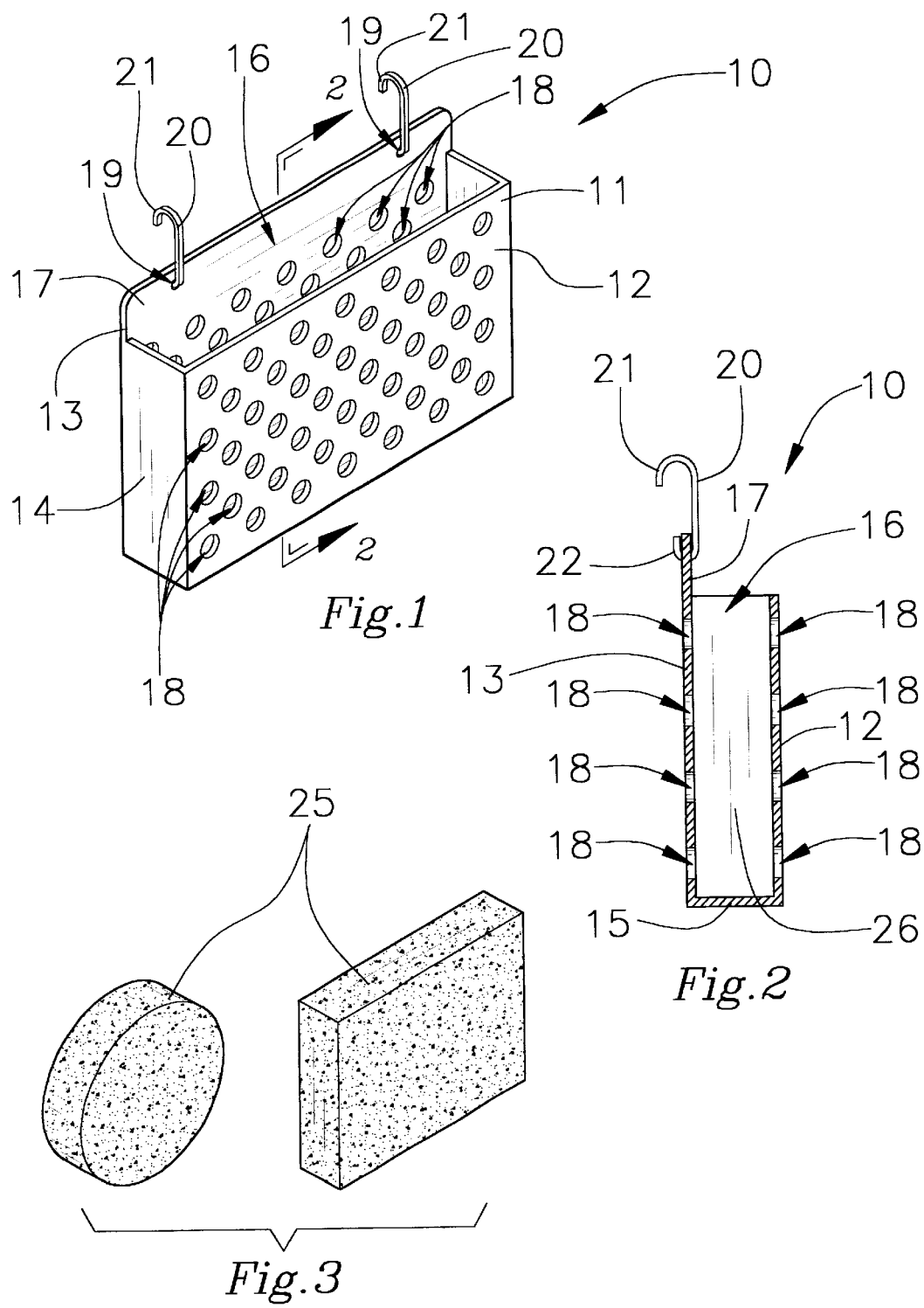

AIR FRESHENER HOLDING DEVICE

BACKGROUND OF THE INVENTION

1. Field of the Invention

The present invention relates to combined air fresheners and more particularly pertains to a new air freshener holding device for evenly dispensing a fragrance throughout an entire room each time a fan unit is turned on.

2. Description of the Prior Art,

The use of combined air fresheners is known in the prior art. More specifically, combined air fresheners heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,624,230; U.S. Pat. No. 5,775,876; U.S. Pat. No. 5,383,765; U.S. Pat. No. 4,944,898; U.S. Pat. No. 4,523,870; and U.S. Pat. No. 5,761,915

While these devices fulfill their respective, particular objectives and requirements, the aforementioned patents do not disclose a new air freshener holding device. The inventive device includes a container having a front wall, a back wall, a bottom wall, side walls, an open top, and a storage compartment being disposed therein and being adapted to removably retain cakes of deodorant; and also includes fastening members being attached to the container and being adapted to attach the container to a fan vent cover.

In these respects, the air freshener holding device according to the present invention substantially departs from the conventional concepts and designs of the prior art, and in so doing provides an apparatus primarily developed for the purpose of evenly dispensing a fragrance throughout an entire room each time a fan unit is turned on.

SUMMARY OF THE INVENTION

In view of the foregoing disadvantages inherent in the known types of combined air fresheners now present in the prior art, the present invention provides a new air freshener holding device construction wherein the same can be utilized for evenly dispensing a fragrance throughout an entire room each time a fan unit is turned on.

The general purpose of the present invention, which will be described subsequently in greater detail, is to provide a new air freshener holding device which has many of the advantages of the combined air fresheners mentioned heretofore and many novel features that result in a new air freshener holding device which is not anticipated, rendered obvious, suggested, or even implied by any of the prior art combined air fresheners, either alone or in any combination thereof.

To attain this, the. present invention generally comprises a container having a front wall, a back wall, a bottom wall, side walls, an open top, and a storage compartment being disposed therein and being adapted to removably retain cakes of deodorant; and also includes fastening members being attached to the container and being adapted to attach the container to a fan vent cover.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new air freshener holding device which has many of the advantages of the combined air fresheners mentioned heretofore and many novel features that result in a new air freshener holding device which is not anticipated, rendered obvious, suggested, or even implied by any of the prior art combined air fresheners, either alone or in any combination thereof.

It is another object of the present invention to provide a new air freshener holding device which may be easily and efficiently manufactured and marketed.

It is a further object of the present invention to provide a new air freshener holding device which is of a durable and reliable construction.

An even further object of the present invention is, to provide a new air freshener holding device which is susceptible of a low cost of manufacture with regard to both materials and labor, and which accordingly is then susceptible of low prices of sale to the consuming public, thereby making such air freshener holding device economically, available to the buying public.

Still yet another object of the present invention is to provide a new air freshener holding device which provides in the apparatuses and methods of the prior art some of the advantages thereof, while simultaneously overcoming some of the disadvantages normally associated therewith.

Still another object of the present invention is to provide a new air, freshener holding device for evenly dispensing a fragrance throughout an entire room each time a fan unit is turned on.

Yet another object of the present invention is to provide a new air freshener holding device which includes a container having a front wall, a back wall, a bottom wall, side walls, an open top, and a storage compartment being disposed therein and being adapted to removably retain cakes of deodorant; and also includes fastening members being attached to the container and being adapted to attach the container to a fan vent cover.

Still yet another object of the present invention is to provide a new air freshener holding device that is easy and convenient to use upon any fan unit having a vent cover.

Even still another object of the present invention is to provide a new air freshener holding device that is more effective than plug-in and stick-on air fresheners.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new air freshener holding device according to the present invention.

FIG. 2 is an end elevational view of the present invention.

FIG. 3 is a perspective view of air fresheners used in the present invention.

DESCRIPTION OF THE PREFERRED EMBODIMENT

Figure 4:
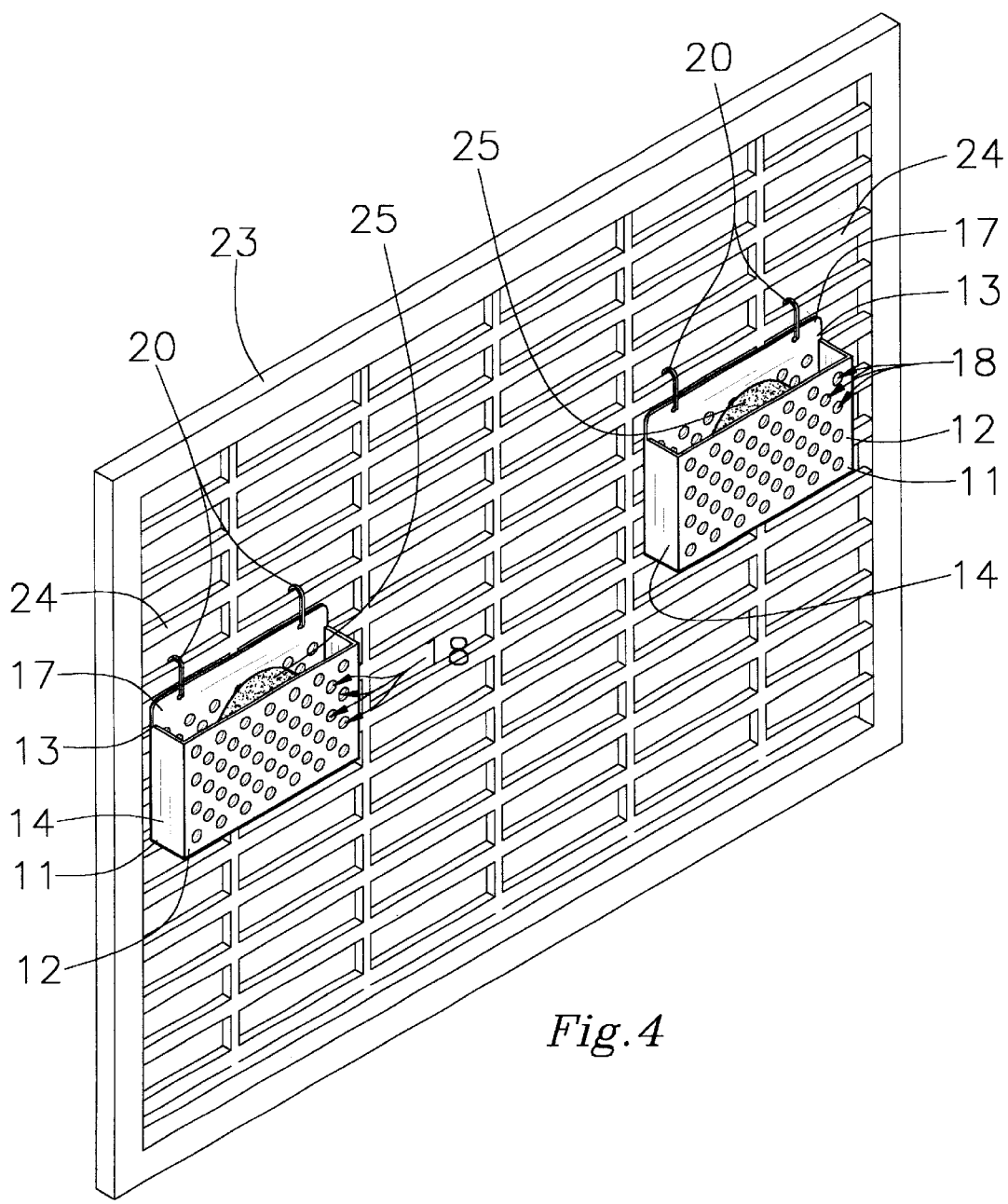
FIG. 4 is a perspective view of the present invention shown in use.

With reference now to the drawings, and in particular to FIGS. 1 through 4 thereof a new air freshener holding device embodying the principles and concepts of the present invention and generally designated by the reference numeral 10 will be described.

As best illustrated in FIGS. 1 through 4, the air freshener holding device 10 generally comprises a container 11 having a front wall 12, a back wall 13, a bottom wall 15, side walls 14, an open top 16, and a storage compartment 26 being disposed therein and being adapted to removably retain cakes of deodorant 25. The front wall 12 and the back wall 13 are essentially made of mesh having a plurality of openings 18 being spaced about and being disposed therethrough. The back wall 13 has a top portion 17 which extends above the side and front walls 12, 14 of the container 11 and also has mounting holes 19 being spaced apart and being disposed through the top portion 17 near a top edge thereof. The container 11 is essentially rectangular shaped with the cakes of deodorant 25 being removably received in the storage container 26 through the open top 16 thereof.

Fastening members are attached to the container 11 and are adapted to attach the container 11 to a fan vent cover 23. The fastening members include hook members 20 each having a curved first end 21 and a curved second end 22 which is removably received in a respective mounting hole 19. The curved first ends 21 are adapted to be hooked about a portion of a grate 24 of the vent cover 23 to essentially suspend the container 11 upon the vent cover 23 to allow air from the fan unit to pass through the openings 18 in the front and back walls 12, 13 of the container 11 and to move a fragrance given off by the cakes of deodorant 25 in the container 11 throughout a room.

In use, the user hooks the curved first ends 21 of the hook members 20 about a portion of a grate 24 of the vent cover 23 to suspend the container 11 upon the vent cover 23, and places one or more cakes of deodorant 25 in the storage compartment 26 through the open top 16, and turns on the fan unit to blow air through the container 11 to effectively move the fragrance given off by the cakes of deodorant 25 throughout the room.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An air freshener holding device comprising:
   a container having a front wall, a back wall, a bottom wall, side walls, an open top, and a storage compartment being disposed therein and being adapted to removably retain cakes of deodorant; and
   fastening members being attached to a vent cover;
   wherein said front wall and said back wall are essentially made of mesh having a plurality of openings being spaced about and being disposed therethrough; and
   wherein said back wall has a top portion which extends above said side and front walls of said container, and also has mounting holes being spaced apart and being disposed through said top portion near a top edge thereof and said fastening members are removably received in a respective said mounting hole.

2. An air freshener holding device as described in claim 1, wherein said fastening members include hook members each having a curved first end and a curved second end which is removably received in a respective said mounting hole, said curved first end being adapted to be hooked about a portion of a grate of the vent cover to essentially suspend said container upon the vent cover to allow air from the fan unit to pass through said openings in said front and back walls of said container and to move a fragrance given off by the cakes of deodorant in said container throughout a room.

3. An air freshener holding device comprising:
   a container having a front wall, a back wall, a bottom wall, side walls, an open top, and a storage compartment being disposed therein and being adapted to removably retain cakes of deodorant, said front wall and said back wall being essentially made of mesh having a plurality of openings being spaced about and being disposed therethrough, said back wall having a top portion which extends above said side and front walls of said container, and also having mounting holes being spaced apart and being disposed through said top portion near a top edge thereof, said container being essentially rectangular shaped with the cakes of deodorant being removably received in said storage container through said open top thereof; and fastening members being attached to a vent cover, said fastening members including hook members each having a curved first end and a curved second end which is removably received in a respective said mounting hole, said curved first end being adapted to be hooked about a portion of a grate of the vent cover to essentially suspend said container upon the vent cover to allow air from the fan unit to pass through said openings in said front and back walls of said container and to move a fragrance given off by the cakes of deodorant in said container throughout a room.

4. An air freshener holding device comprising:

a container having a front wall, a back wall, a bottom wall, side walls, an open top, and a storage compartment being disposed therein and being adapted to removably retain cakes of deodorant; and fastening members being attached to a vent cover; wherein said front wall and said back wall comprise mesh having a plurality of openings being disposed therethrough; and wherein said back wall has a top portion which extends above said side and front walls of said container, and said back wall has mounting holes being spaced apart and being disposed through said top portion near a top edge thereof and said fastening members are removably received in a respective said mounting hole.

5. An air freshener holding device as described in claim 1, wherein said fastening members include hook members each having a curved first end and a curved second end which is removably received in a respective said mounting hole, said curved first end being adapted to be hooked about a portion of a grate of the vent cover to essentially suspend said container upon the vent cover to allow air from the fan unit to pass through said openings in said front and back walls of said container and to move a fragrance given off by the cakes of deodorant in said container throughout a room.

* * * * *